US010751216B2

(12) United States Patent
Bach et al.

(10) Patent No.: US 10,751,216 B2
(45) Date of Patent: Aug. 25, 2020

(54) REMOTE OPTHALMIC SYSTEM AND RELATED METHODS

(71) Applicant: TYB LLC, Miami Beach, FL (US)

(72) Inventors: Austin E. Bach, Miami Beach, FL (US); Melissa Morris, Boca Raton, FL (US)

(*) Notice: Subject to any disclaimer, the term of this patent is extended or adjusted under 35 U.S.C. 154(b) by 212 days.

(21) Appl. No.: 15/689,343

(22) Filed: Aug. 29, 2017

(65) Prior Publication Data

US 2017/0360604 A1 Dec. 21, 2017

Related U.S. Application Data

(63) Continuation-in-part of application No. PCT/US2016/030910, filed on May 5, 2016.

(60) Provisional application No. 62/158,207, filed on May 7, 2015.

(51) Int. Cl.
| *A61F 9/008* | (2006.01) |
| *A61B 34/35* | (2016.01) |
| *A61B 34/30* | (2016.01) |
| *A61B 34/00* | (2016.01) |

(52) U.S. Cl.
CPC .............. *A61F 9/008* (2013.01); *A61B 34/30* (2016.02); *A61B 34/35* (2016.02); *A61B 2034/742* (2016.02); *A61F 2009/00878* (2013.01)

(58) Field of Classification Search
CPC .................................. A61F 9/008; A61F 9/009
USPC .......................................................... 606/4–5
See application file for complete search history.

(56) References Cited

U.S. PATENT DOCUMENTS

| 5,368,015 A | 11/1994 | Wilk |
| 5,855,553 A | 1/1999 | Tajima et al. |
| 6,139,542 A | 10/2000 | Hohla |
| 7,325,923 B2 | 2/2008 | Makino |
| 7,520,611 B2 | 4/2009 | Franz et al. |
| 7,818,041 B2 | 10/2010 | Kim et al. |
| 7,846,150 B2 | 12/2010 | Hamel et al. |
| 8,075,552 B2 | 12/2011 | Kurtz et al. |
| 8,833,941 B2 | 9/2014 | Wei et al. |
| 8,866,870 B1 | 10/2014 | Smith |
| 8,903,468 B2 | 12/2014 | Peyman |
| 2003/0035084 A1 | 2/2003 | Makino |
| 2003/0208189 A1 | 11/2003 | Payman |
| 2004/0054358 A1 | 3/2004 | Cox et al. |

(Continued)

FOREIGN PATENT DOCUMENTS

| JP | 5083758 | 11/2012 |
| WO | WO9746183 | 12/1997 |

*Primary Examiner* — Lynsey C Eiseman
(74) *Attorney, Agent, or Firm* — Allen, Dyer, Doppelt & Gilchrist, PA

(57) ABSTRACT

A remote ophthalmic system may include an examination device having an ophthalmic laser device, and a first processor coupled to the ophthalmic laser device, a communication network, and a remote control device being associated with a user, being remote to the examination device, and being in communication with the examination device over the communication network. The first processor may be configured to receive target values for application of the ophthalmic laser device from the remote control device, the target values for application of the ophthalmic laser device being associated with an ophthalmic procedure on a patient, and perform the ophthalmic procedure on the patient by applying the ophthalmic laser device based upon the target values.

19 Claims, 13 Drawing Sheets

(56) References Cited

U.S. PATENT DOCUMENTS

| | | | |
|---|---|---|---|
| 2007/0173793 A1* | 7/2007 | Rathjen | A61F 9/008 606/4 |
| 2008/0234666 A1 | 9/2008 | Yadlowsky et al. | |
| 2010/0145320 A1 | 6/2010 | Horvath et al. | |
| 2012/0316544 A1* | 12/2012 | Horvath | A61F 9/00825 606/6 |
| 2013/0110093 A1 | 5/2013 | Yee | |
| 2014/0139805 A1 | 5/2014 | Carnevale | |
| 2014/0257259 A1* | 9/2014 | Papastathopoulos | A61F 9/00825 606/4 |

* cited by examiner

REMOTE OPTHALMIC SYSTEM AND RELATED METHODS

This application claims priority from prior filed copending Patent Cooperation Treaty Application No. PCT/US16/30910 filed May 5, 2016, which claims the priority benefit of provisional application Ser. No. 62/158,207 filed on May 7, 2015, the entire contents of both are herein incorporated in its entirety by reference.

TECHNICAL FIELD

The present disclosure relates to the field of remote medical devices, and, more particularly, to a remote ophthalmic system and related methods.

BACKGROUND

Surgical procedures on the human eye are becoming more common as medical devices and associated technology improve. Even with this enhanced ability to perform a plethora of surgical procedures, there is still a lack of access to care. Remote ophthalmic treatment of disease enables specialists in the field of ocular disease to treat patients that have less access to care. It also enables faster, more accurate, and more precise treatment of ocular disease including, but not limited to open and closed angle glaucoma, diabetes, and retinal tears. This type of diagnosis and treatment cannot be done remotely without having full control of an imaging and illuminating device as well as a direct/indirect contact laser/gonioscopy lens.

SUMMARY

Generally speaking, a remote ophthalmic system may comprise an examination device comprising an ophthalmic laser device, and a first processor coupled to the ophthalmic laser device. The remote ophthalmic system may comprise a communication network, and a remote control device being associated with a user, being remote to the examination device, and being in communication with the examination device over the communication network. The first processor may be configured to receive a plurality of target values for application of the ophthalmic laser device from the remote control device, the plurality of target values for application of the ophthalmic laser device being associated with at least one ophthalmic procedure on a patient, and perform the at least one ophthalmic procedure on the patient by applying the ophthalmic laser device based upon the plurality of target values. Advantageously, the user may perform a wide variety of ophthalmic procedures on the patient remotely.

More specifically, the examination device may comprise an image sensor device coupled to the first processor and configured to generate image data associated with an eye of the patient. The first processor may be configured to transmit the image data to the remote control device. The remote control device may comprise a display, and a second processor coupled to the display. The second processor may be configured to receive the image data, and display the image data on the display.

In some embodiments, the remote control device may include a user input interface coupled to the second processor. The second processor may be configured to generate the plurality of target values for application of the ophthalmic laser device based upon input from the user input interface. The user input interface may comprise a directional input, at least one video feed, and a plurality of control inputs.

Moreover, the examination device may include at least one robotic arm coupled to the first processor, and a lens coupled to a distal end of the at least one robotic arm. The first processor may be configured to position the lens via the at least one robotic arm. The first processor may be configured to position the lens based upon input from the remote control device. The first processor may be configured to receive at least one laser parameter for the plurality of target values for application of the ophthalmic laser device from the remote control device. The at least one laser parameter may comprise a pulse type and pulse duration.

Another aspect is directed to a method for making a remote ophthalmic system. The method may include providing an examination device comprising an ophthalmic laser device, and a first processor coupled to the ophthalmic laser device. The method may include providing a remote control device to be associated with a user, to be remote to the examination device, and to be in communication with the examination device over a communication network. The first processor may be configured to receive a plurality of target values for application of the ophthalmic laser device from the remote control device, the plurality of target values for application of the ophthalmic laser device being associated with at least one ophthalmic procedure on a patient, and perform the at least one ophthalmic procedure on the patient by applying the ophthalmic laser device based upon the plurality of target values.

DETAILED DESCRIPTION

Figure 1:
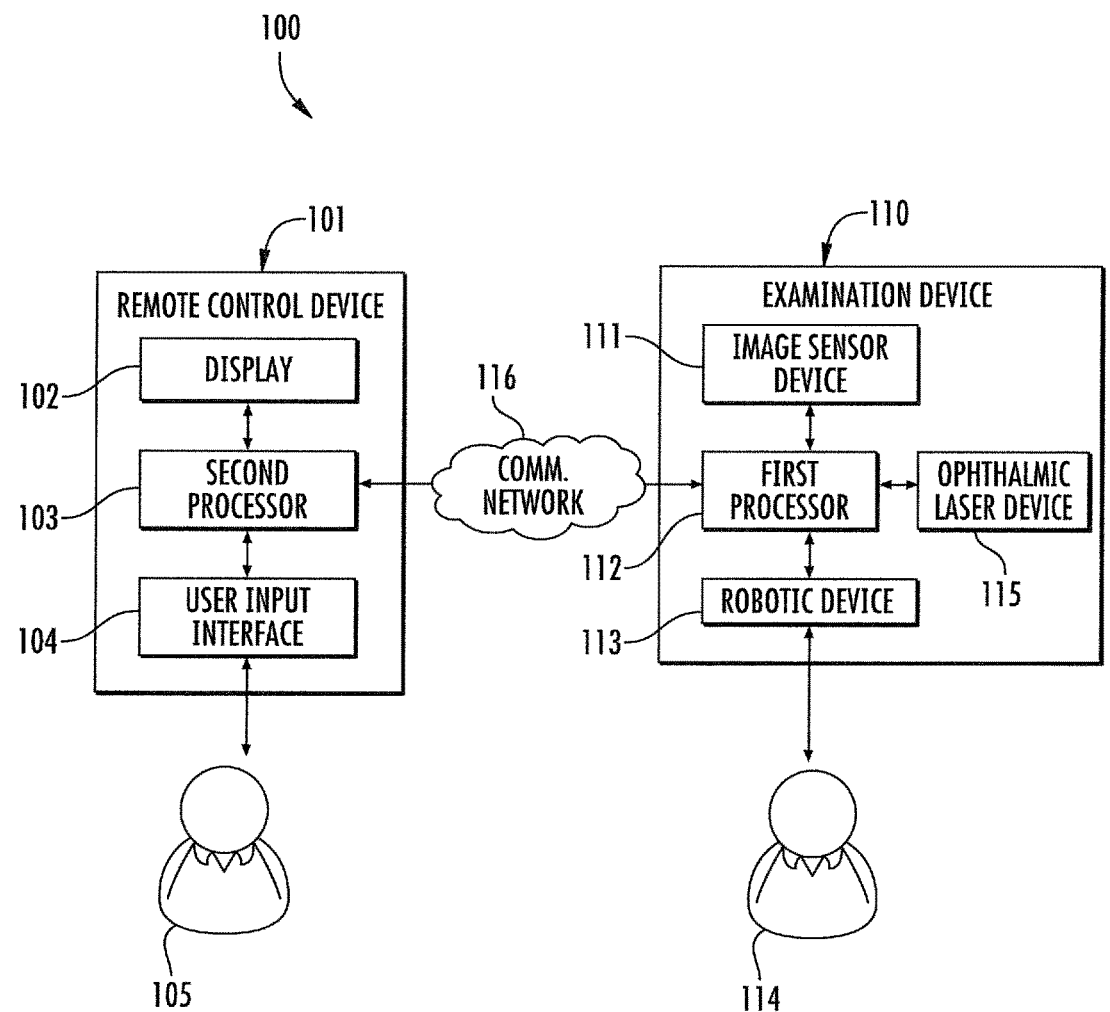
FIG. 1 is a schematic diagram of a remote ophthalmic system, according to the present invention.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Generally speaking, a remote ophthalmic system may comprise an examination device comprising an imaging system, an illuminating system, an ophthalmic lens holder, and ophthalmic laser device, and a first processor coupled to the imaging system, illuminating system, lens holder, and ophthalmic laser device. The remote ophthalmic system may comprise a communication network, eye tracking software, and a remote control device being associated with a user, being remote to the examination device, and being in communication with the examination device over the communication network enabling a full range of movement of said examination device. The first processor may be configured to receive a plurality of target values for application of laser treatment of the ophthalmic laser device from the remote control device, the plurality of target values for application of laser treatment from the ophthalmic laser device being associated with at least one ophthalmic procedure on at least one intra- or extraocular structure of the eye of a patient, and perform the at least one ophthalmic procedure on the intra- or extraocular structure of the eye of the patient by applying laser treatment via the ophthalmic laser device based upon the plurality of target values. Advantageously, the user may perform a wide variety of ophthalmic procedures on the patient, remotely.

More specifically, the examination device may comprise an image sensor device coupled to the first processor and configured to generate image data, both video and still-frame, associated with both internal and external imaging data of the associated with an eye of the patient. The first processor may be configured to transmit the image data to the remote control device. The remote control device may comprise a display, and a second processor coupled to the display. The second processor may be configured to receive the image data, and display the image data on the display.

In some embodiments, the remote control device may include a user input interface coupled to the second processor. The second processor may be configured to generate the plurality of target values for application of laser treatment via the ophthalmic laser device based upon input from the user input interface. The user input interface may comprise a directional input, at least one video feed, and a plurality of control inputs.

Moreover, the examination device may include at least one robotic arm coupled to the first processor, and an ophthalmic lens holder coupled to a distal end of the at least one robotic arm. The first processor may be configured to position the ophthalmic lens in the lens holder via the at least one robotic arm. The first processor may be configured to position the lens based upon input from the remote control device. The first processor may be configured to receive at least one laser parameter for the plurality of target values for application of a laser treatment via the ophthalmic laser device from the remote control device, potentially through the ophthalmic lens. The at least one laser parameter may comprise a pulse type and pulse duration.

Another aspect is directed to a method for making a remote ophthalmic system. The method may include providing an examination device comprising a slit lamp biomicroscope or imaging system, an ophthalmic lens holder, an ophthalmic laser device, and a first processor coupled to the imaging system, illuminating system, an ophthalmic lens holder, and ophthalmic laser device. The method may include providing a remote control device to be associated with a user, to be remote to the examination device, and to be in communication with the examination device over a communication network. The first processor may be configured to receive a plurality of target values for application of laser treatment via the ophthalmic laser device from the remote control device, the plurality of target values for application of laser treatment via the ophthalmic laser device being associated with at least one ophthalmic procedure on at least one intra- or extraocular structure of the eye of a patient, and perform at least one ophthalmic procedure on at least one intra- or extraocular structure of the eye of the patient by applying laser treatment via ophthalmic laser device based upon the plurality of target values.

Figure 2A:
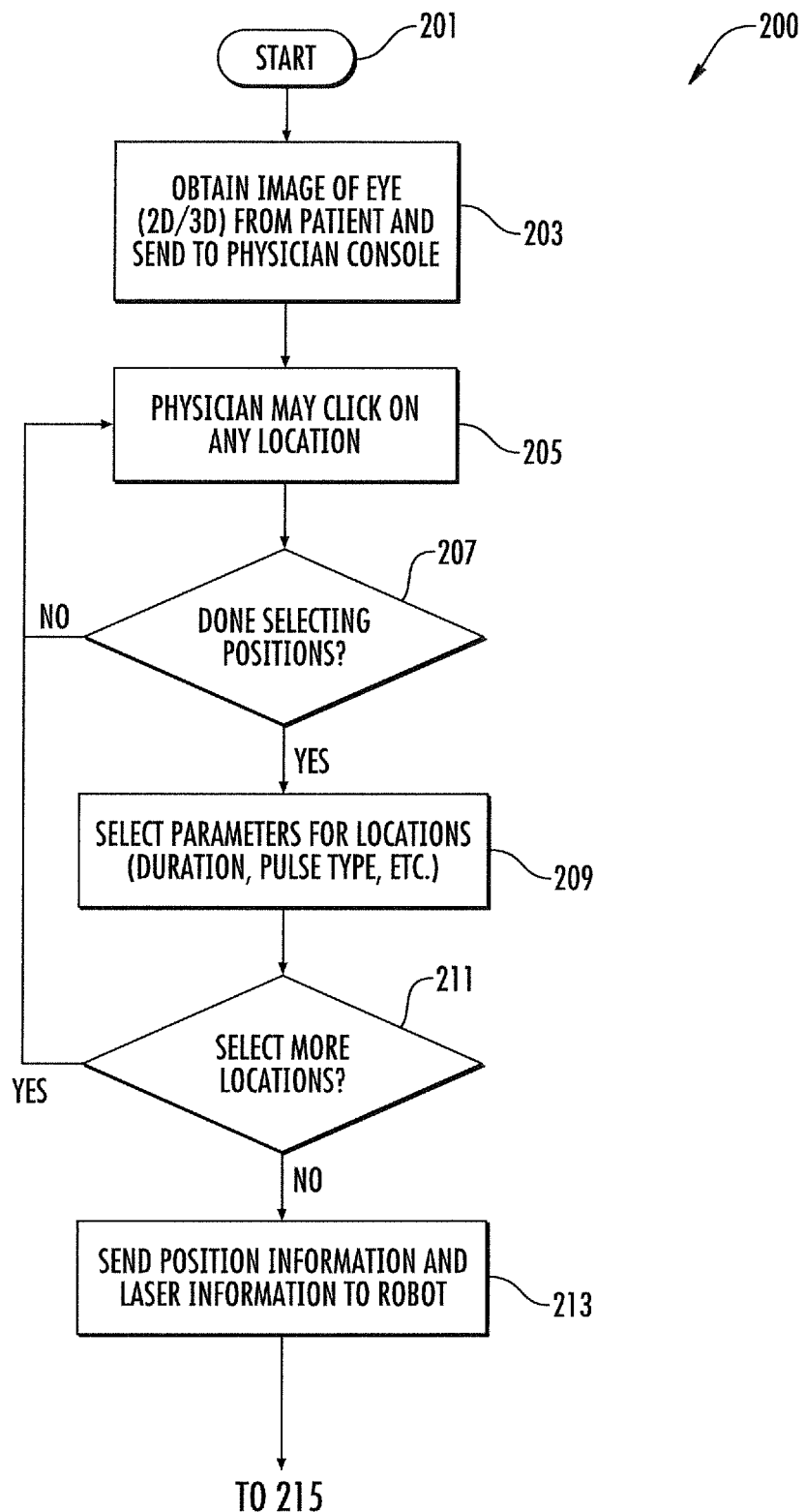
FIGS. 2A-2B are flowcharts illustrating operation of the remote ophthalmic system of FIG. 1.
Figure 2B:
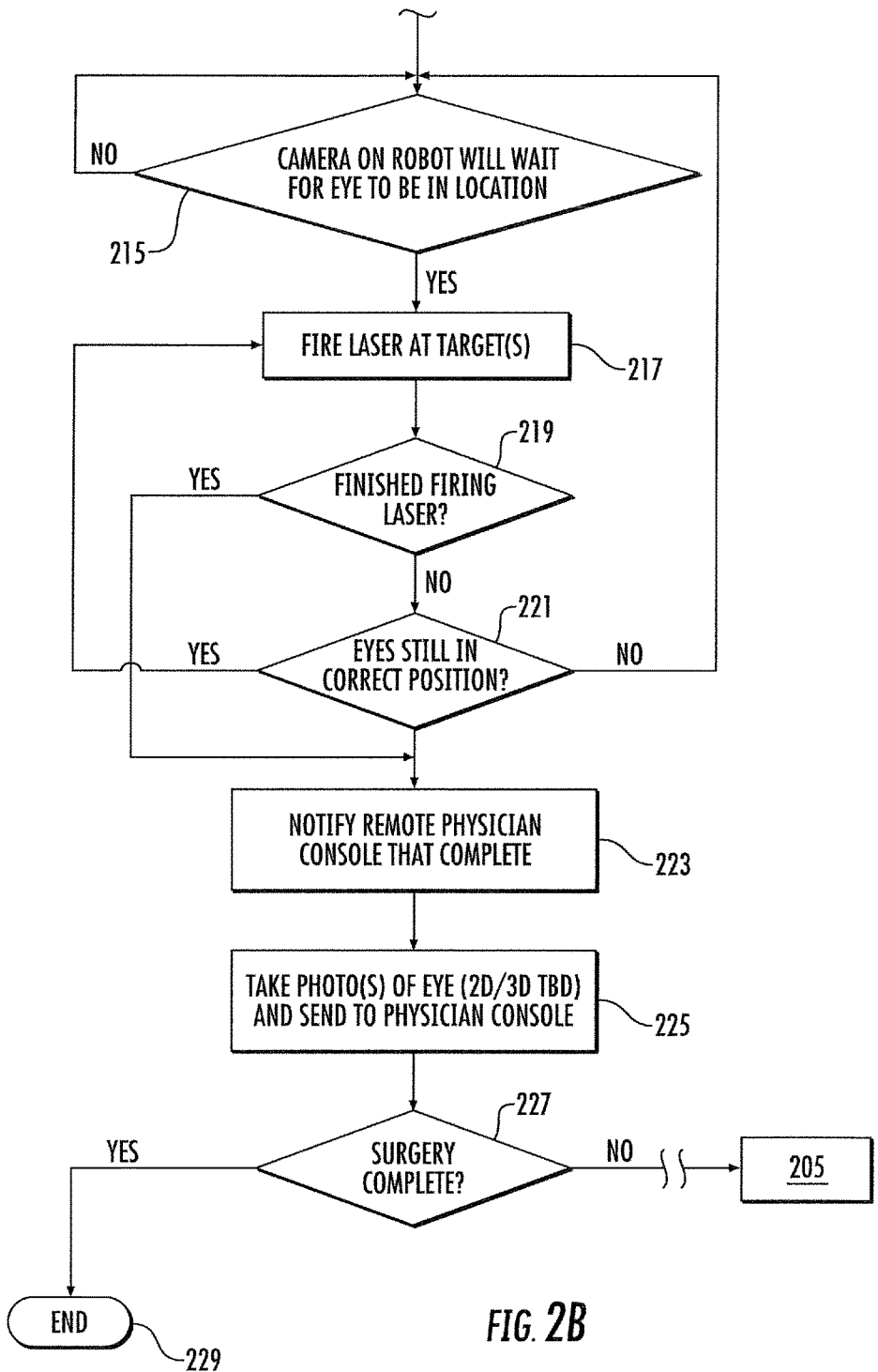

Referring initially to FIGS. 1-2B, a remote ophthalmic system 100 according to the present invention is now described. With reference to flowchart 200, a method for operating the remote ophthalmic system 100 is also now described. The remote ophthalmic system 100 permits a user (i.e. doctor) 105 to remotely examine and perform ophthalmic procedures on a patient 114.

The remote ophthalmic system 100 illustratively includes an examination device 110, and a remote control device 101 physically separated from and remote to the examination device. The remote control device 101 is coupled to the examination device 110 over a communication path, such as a networked connection, e.g. internet, cellular, closed wired or wireless local area network (LAN/WLAN). The remote control device 101 illustratively includes a display 102, a second processor 103 coupled to the display, and a user input interface (e.g. control pad, mouse device) 104 coupled to the processor.

The remote control device 101 may comprise a computer programmed with software from the teachings herein, or other devices that can remotely control the remote ophthalmic system. In some embodiments (FIG. 5), the user input interface 104 can comprise a full scale slit lamp device, i.e. operating as a clone device for the examination device version.

The examination device 110 illustratively includes a first processor 112, an image sensor device (e.g. high definition video sensor, 4k video sensor) 111 coupled to the processor, and a robotic device 113 coupled to the processor and adjacent to the patient 114. During typical use of the remote ophthalmic system 100, the display 102 receives the output of the image sensor device 111, and the user 105 manipulates the user input interface 104 for controlling the robotic device 113 to perform the procedure. Advantageously, the user 105 is able to perform the procedure on the patient 114 from a remote location.

In some embodiments (FIG. 3), the robotic device 113 may comprise a slit lamp device 30. The slit lamp device 30 illustratively includes a plurality of control mechanisms 24 (e.g. typical knobs for adjusting the slit lamp device), a support 32 for receiving the patient's chin, and an optical lens holder (e.g. gonioscopy lens, transequator lens) aligned with the patient's eyes. This optical lens holder may be attached to the robotic device 113 at one or multiple sites. In the slit lamp device 30, the image sensor device 111 is aligned with an output of the optical lens holder. Also, the slit lamp device 30 includes a plurality of motors actuating the corresponding plurality of control mechanisms, thereby providing the user 105 complete control.

In some embodiments, the slit lamp device 30 includes an optical source 115 (e.g. a surgical laser, such as an Argon or solid state laser), and the user input interface 104 permits control of the optical source (e.g. generating a plurality of laser pulses). Accordingly, the user 105 may remotely adjust the slit lamp device 30, examine the eyes of the patient 114, both intraocularly and extraocularly, and perform the procedure. In some embodiments, the slit lamp device 30 may also include a plurality of robotic arms 22 with respective surgical tools (e.g. laser eye surgery tools, such as additional lens holders or lens) thereon. In these embodiments, the user 105 may perform more complex procedures or surgeries from the remote location.

Figure 3:
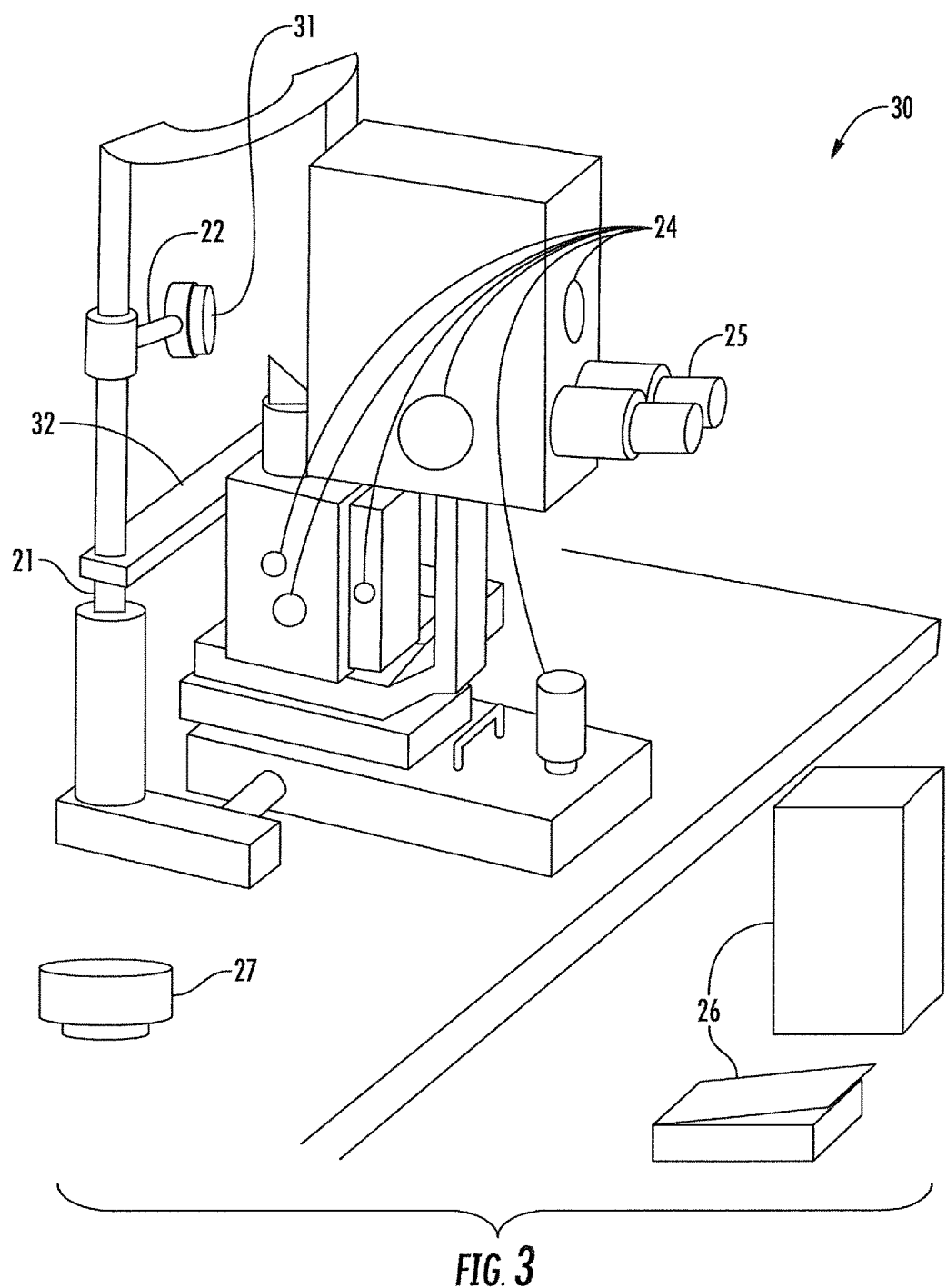
FIG. 3 is a perspective view of an embodiment of the examination device.

In the embodiment of FIG. 3, the slit lamp device 30 comprises a robotic arm 22 coupled to the slit lamp device and for holding and positioning a lens 31 (e.g. gonioscopy lens, transequator lens) that directs a laser beam into portions of the patient's eye (i.e. the retina, the iridocorneal angle and any place else in and around the eye) that may or may not be visible without said lens. The remote control device 101 may control the robotic arm 22. In addition, the remote control device 101 operates a software interface on the display 102 that enables the user 105 to select individual or a plurality of applications of the laser (i.e. individual pulse selection). In some embodiments, the user 105 selects the individual applications of the laser, and upon execution, the examination device 110 performs the individual applications without further input from the user. In other embodiments, the user 105 could manually select each position for near instantaneous laser application, i.e. a manual mode.

Indeed, in some embodiments, the user 105 is provided a detailed image of the patient's eye, intraocular and/or extraocular structures, on the display 102, and the user can individually select positions and parameters for application of the laser. The parameters can comprise laser pulse power, laser pulse duration, and laser pulse type. Once a plurality of individual or multiple applications has been selected, the remote control device 101 directs the laser to complete the plurality of individual applications.

In addition, the remote control device 101 operates eye tracking functions using the image sensor device 111. The remote control device 101 automatically adjusts the plurality of individual applications based upon eye tracking feedback. The optical system can be used in a wide range of ophthalmic procedures, such as in Laser Trabeculoplasty or retinal laser surgery, for example. In some embodiments, the examination device 110 may include a light source (not shown) configured to illuminate the eye of the patient 114 during the procedure.

With reference to flowchart 200, the method for operating the remote ophthalmic system 100 begins at Block 201, and includes obtaining an image of the patient's eye, which is sent to the display of the remote control device 101 (Block 203). The user 105 then selects laser application locations, and laser parameter settings (Blocks 205, 207, 209, 211). Once complete, the laser application locations and the parameter settings are transmitted to the examination device 110 (Block 213). Once the patient's eye is properly positioned and tracked, the laser begins the laser firing process (Blocks 215, 217, 219, 221). In Block 221, the examination device 110 is looking for proper positioning of the patient's eye via the image sensor device 111. If the patient's eye is out of position, the laser firing process is automatically halted until the eye tracking software determines the position of the patient's eye to be that which was originally imaged. Once the laser firing process is complete, the user 105 is notified at Block 223, and the user receives a final image of the patient's eye (Blocks 225, 227, 229).

Referring now to FIGS. 3-6, an exemplary discussion of the remote ophthalmic system 100 now follows.

INTRODUCTION

The proposed device is a robotic slit-lamp (or slit-lamp-like device, not specifically shown here) under the direction of an ophthalmologist using a control console. The control console could be in the same room; however, it is expected that it will more typically be located at a remote location from the patient. The patient will be seated at the slit-lamp similarly as in-person slit-lamp examinations and procedures. At least one trained attendant will be assisting at the location with the robot and patient. The device will be capable of performing eye examinations as well as certain laser surgeries.

Possible Benefits Include:
(a) increased accuracy, increased speed, and increased precision of certain laser eye surgeries
(b) increased access to eye care for patients in remote and impoverished areas
(c) specialist access to and from nearly any location
(d) increased ergonomics of laser surgery planning and execution
(e) decreased travel for physicians covering large geographical areas
(f) decreased travel for patients in rural areas
(g) ability to monitor or record procedures for training or evaluation purposes Device Features
Robotic Device (Patient-Side)

The main components of the patient-side device are shown in FIG. 3. The patient will sit upright and place his/her head against the headrest shown on the left of FIG. 3. The patient's chin will rest on the chin bar and forehead on the upper brace. The chin bar height is adjusted via a screw mechanism 21. This can be manually performed by the onsite assistant as done with non-robotic slit-lamps, or as an added option in another embodiment will allow the physician to control this via an electronic actuator. This will align the eyes vertically for all procedures and eyes should be in-line with the lens holder.

The lens holder will be initially placed out of the way. When needed, it can be swung into the position shown. The end of the lens holder will have a manual clip for the on-site assistant to insert the desired lens 31 for focusing on different parts of the eye that may or may not be visible without the lens. It will likely be tightened similarly as a band clamp or quick lock clamp (such as those used on pipes in the automotive industry), via a twist-lock (i.e. keyless chuck) mechanism (such as those used to secure bits inside drill chucks) or via set screws. In addition to being able to be pivoted, the lens holder may also have horizontal and vertical adjustments (likely via a screw mechanism) along the arm to fully align the lenses over the eye. Large adjustments can be manually performed by the assistant, but the physician will electronically actuate these functions for precise placement. There may be a lens holder on each side of the headrest or one placed strategically so that procedures may be done on either eye.

All rotating parts of the device will be fitted with accurate electronic actuators to allow the position of both the laser and the imaging system and illuminating system to be independently adjusted. Their position can be directly controlled by the physician or computer-controlled depending on the procedure being performed and the physician's preference. All necessary manual adjustment knobs 24 will be additionally electronically actuated to allow for remote-control of key features of the device. Only knobs that mechanically control features will be actuated, not necessarily all knobs shown in FIG. 3. These knobs may not appear on the outside of the slit-lamp if on-site control is not desired, but are shown in the figure for representation. The full binocular microscope 25 is not necessary, though is shown in FIG. 3 so the appearance of a slit-lamp is maintained. The internal microscope portion is needed and a high-resolution digital video camera will be mounted to the slit-lamp. In some embodiments, the internal microscopic portion could be omitted if included in the camera apparatus.

A manual laser controller 26 may remain on-site with the foot pedal or trigger button 10 optionally connected. The physician will be able to determine whether any on-site control features remain active during the procedures. Typically, all physical on-site laser triggers will be deactivated and removed to avoid inadvertent activation by untrained individuals. For added safety, an emergency stop button 27 will be placed in an easily accessible location near the on-site assistant. The emergency stop button will immediately disconnect all power to the laser and actuated components. The emergency stop button is needed in the event of a robot malfunction or an on-site event requires that the procedure be immediately halted. Communication lines and video feed will remain active, however.

Communication

Figure 4:
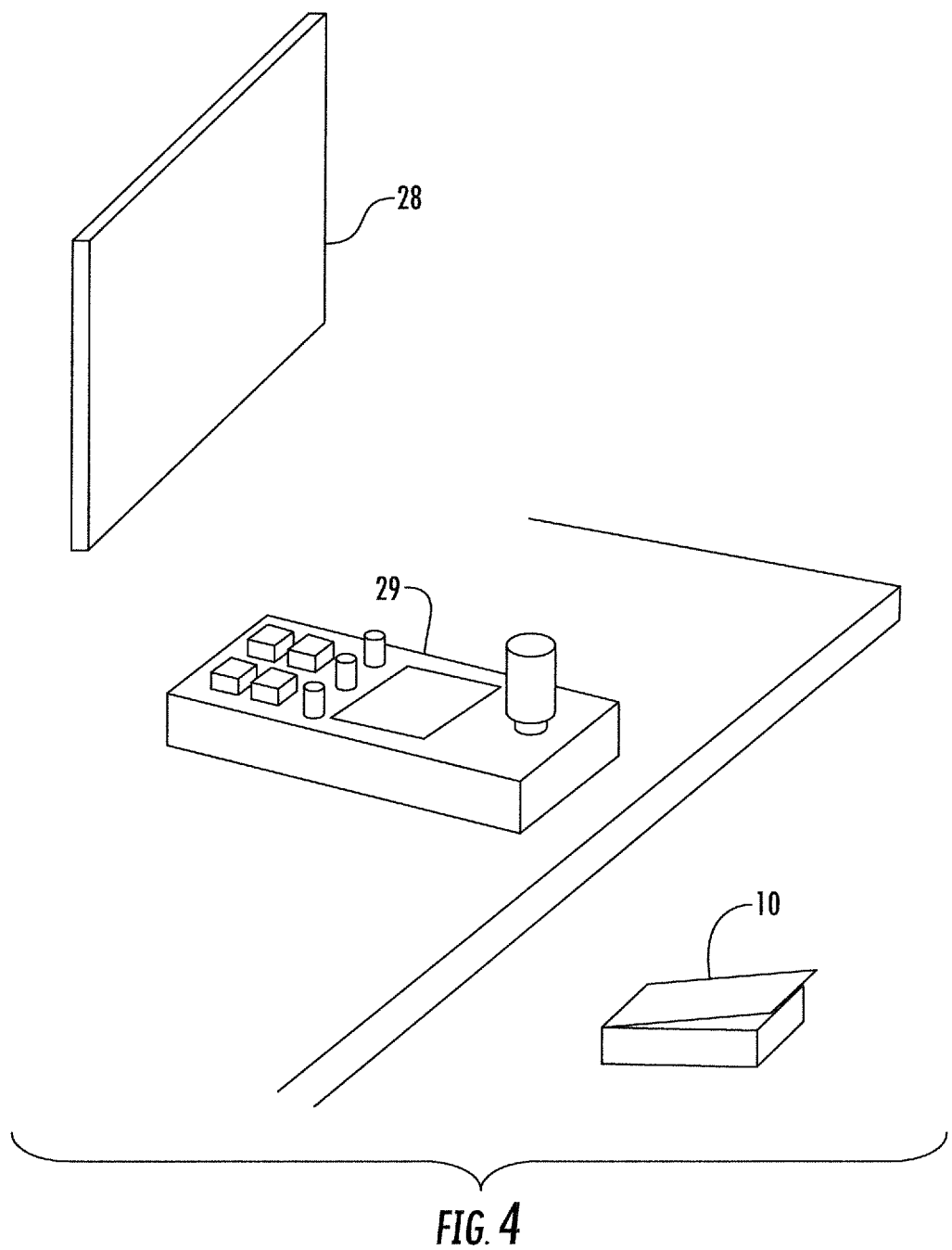
FIG. 4 is a perspective view of an embodiment of the remote control device.
Figure 5:
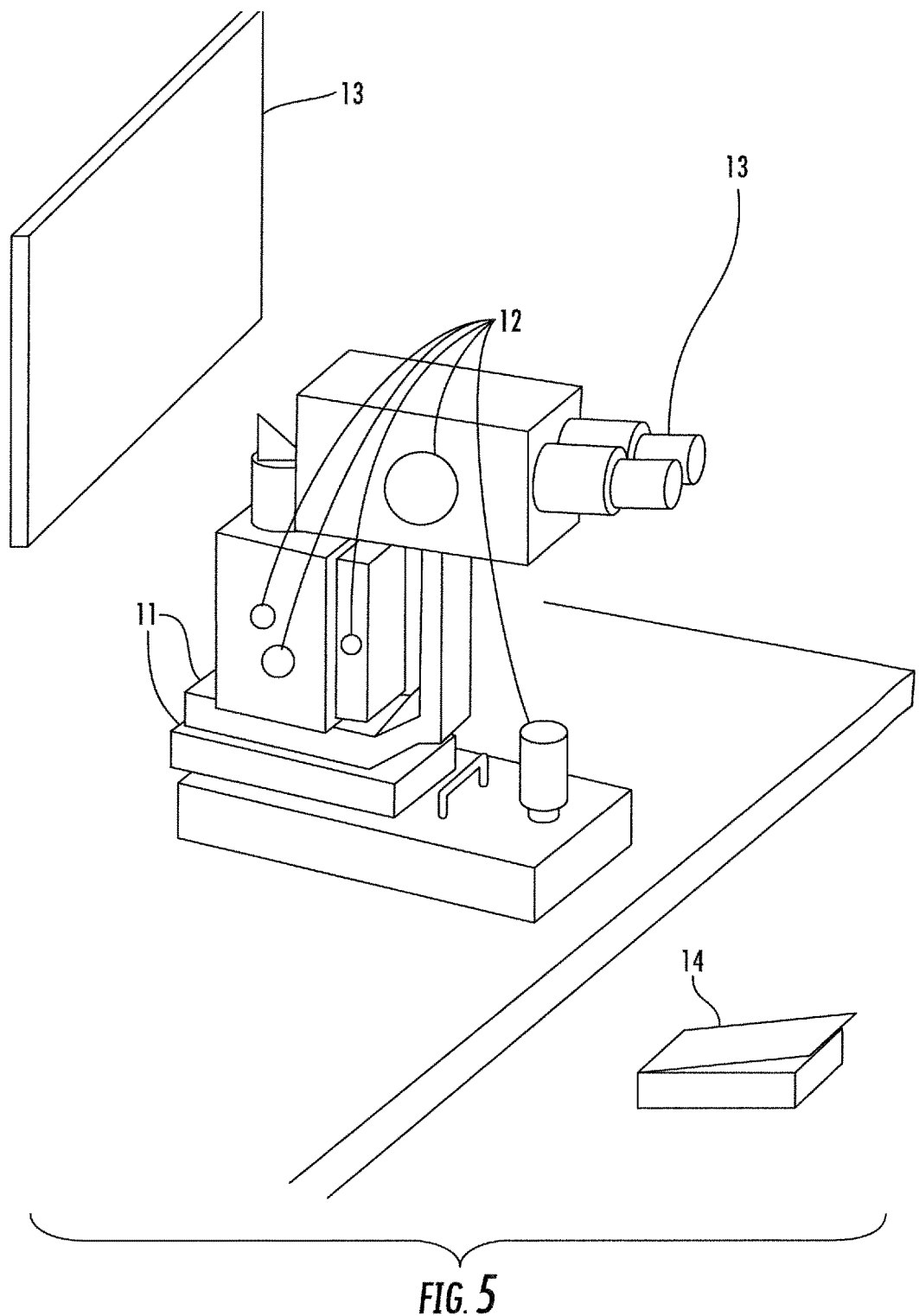
FIG. 5 is a perspective view of another embodiment of the remote control device.

Not shown in FIGS. 3-5 are the communication connections between the robot and the physician console. Existing lines of communication will be used and can include direct wires, WiFi, Bluetooth, telephone lines, cable lines, cellular connections, satellite connection or any other forms of communication existing now or in the future. Any one or multiple methods of communication may be used pending the locations, desired use of a back-up and bandwidth requirements.

The communication lines will transmit bi-directional audio feed, video feed (minimally from the patient to the physician, bi-directional feed is optional), control instructions from the physician's console to the robot, and sensor information and feedback from the robot to the physician. The audio feed is necessary so that the physician can quickly communicate with the patient and assistant (though visual text-based communication could also be used). Appropriate hardware, such as microphones and speakers, is needed on both sides to facilitate this communication. None of these features will be novel, however.

Physician Console

There are two possible physician-side console options currently proposed. The first, shown in FIG. 4, is simpler and best when low-cost or portability are priorities. This design includes a monitor 28 that is of sufficient size and resolution for the physician to easily view the transmitted video feed sent from the robotic slit-lamp. The transmitted video may comprise one or more of two-dimensional (2D) data and three-dimensional (3D) data.

The control console 29 can comprise any combination of input mechanisms such as buttons, switches, joysticks, track pads, touch screens, etc. FIG. 4 shows a representation of various types of input mechanisms and not the actual final version of this console. The console could also be simply a computer mouse allowing the physician to "point and click" on a computer screen to select laser target areas and menu options.

Another option is to use a tablet computer or a touch screen monitor 28 for implementing controls in this way. Software buttons and dials, "soft keys," can appear on the monitor or tablet screen to allow for selecting various options during use. The use of a foot pedal or dedicated "hard" trigger button 14 for the laser is optional and may provide a layer of comfort when activating the laser. It provides a different type of motion to ensure the laser is activated only when the physician is ready. Additional software checks will be in place to prevent most accidental laser triggers.

The second physician console option is shown in FIG. 5. This would be more familiar in use to physicians as it is similar to a slit-lamp. The physician would operate the master slit lamp on his/her end to control the slave device at the patient's location. It is desirable that the master and slave slit-lamps be very similar, if not identical, in size and positioning of the key components such as the slit-illuminator. The master slit-lamp has position sensors 11 located on all moving joints. Information can be read from these sensors and transmitted to the slave device to perform the same motion via electronic actuators or stored in memory to execute a task at a later time.

Control knobs also have position sensors 12 that transmit information to the slave device so that controls on the robotic device can be adjusted to the same setting. The physician may chose to use a regular monitor or binoculars 13. The monitor is more ergonomic for performing remote procedures or surgeries, so the binoculars on the master device are not needed and are optional. However, by installing small displays into the binoculars, the device could potentially be used as a training tool or to provide 3D visual feedback without a specialized 3D monitor.

Software

The software will include necessary aspects for control of the robotic device. It will be able to translate points selected on a picture of the eye to physical positions of the robotic device to direct illuminating device, imaging device, and the laser to those points on the actual eye. It will also include all necessary components for providing communication between the robot and physician's console.

In some embodiments, due to the unavoidable delay in remote control, the software will monitor eye position. It should be noted that the patient's body/head will not be immobilized and the patient will also be able to freely move his/her eyes. From the control console, the physician will select a point (or multiple points) in the eye (for each point). Also, the duration, type, power, size, as well as any other parameters, are adjustable for the laser by the physician console or at the site by the assistant. When commanded, the robotic device will only fire the laser during times that the eye is in the desired position(s) and otherwise wait. After all targets have been lasered, the physician will be notified that the task is complete and can inspect the progress. The software will allow for different modes of operation. The robot can move in real-time with the slave device (or control inputs pending the console style used). In addition, the robot can automatically move after a desired task has been fully "programmed." The software allows for recording of images or video. Split screens showing former and current images or video can be used for various evaluation needs. In another embodiment where the laser tracking speed is increased, the laser can fire in real time and compensate for movement of the eye without pausing.

Referring now again to FIG. 1, a remote ophthalmic system 100 illustratively includes an examination device 110 comprising an ophthalmic laser device (e.g. an argon laser) 115, and a first processor 112 coupled to the ophthalmic laser device. The examination device 110 may have a slit lamp device form factor (i.e. Zeiss-Style, Haag-Streit Style, or portable/hand-held), or be a modified version with and illuminating and imaging system, for example. In some embodiments, the ophthalmic laser device 115 can be omitted in the examination device 110.

The remote ophthalmic system 100 illustratively includes a communication network (e.g. the Internet, a cellular network, or a closed local area network, etc.) 116, and a remote control device 101 being associated with a user 105, being remote (e.g. another room in a same facility, or several miles away) to the examination device 110, and being in communication with the examination device over the communication network. The first processor 112 is configured to receive a plurality of target values for application of the ophthalmic laser device 115 from the remote control device 101, the plurality of target values (i.e. positional values within an eye of a patient 114) for application of the ophthalmic laser device being associated with at least one ophthalmic procedure on the patient, and perform the at least one ophthalmic procedure on the patient by applying the ophthalmic laser device based upon the plurality of target values.

More specifically, the examination device 110 illustratively includes an image sensor device 111 coupled to the first processor 112 and configured to generate image data (e.g. three-dimensional voxel image data or two-dimensional image data) associated with an eye of the patient 114, and the first processor is configured to transmit the image data to the remote control device 101. The remote control device 101 illustratively includes a display 102, and a second processor 103 coupled to the display. The second processor 103 is configured to receive the image data, and display the image data on the display 102. For example, the first and second processors 112, 103 may comprise application specific integrated circuits, or field-programmable gate array (FPGA) integrated circuits configured with the teachings herein.

Figure 14:
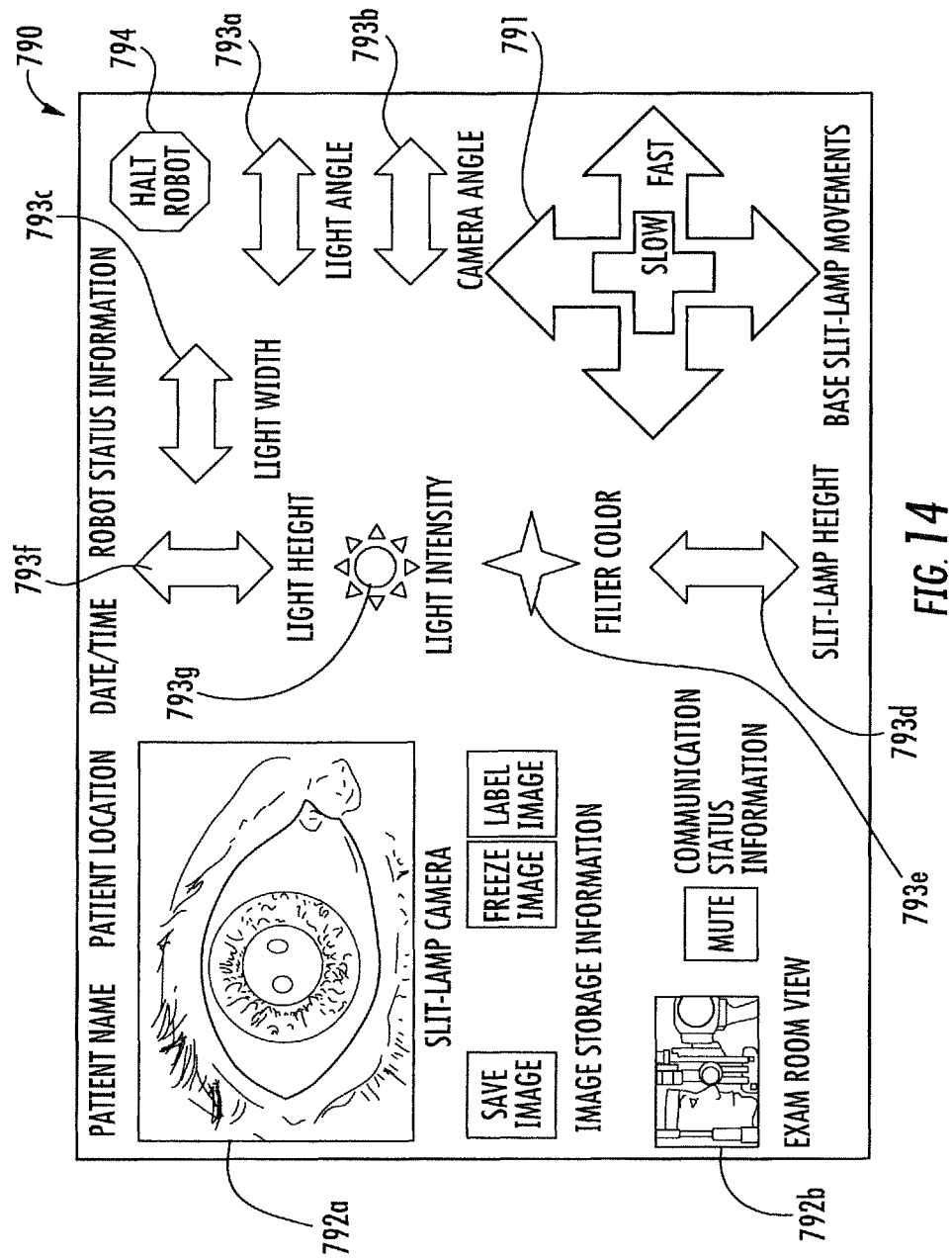
FIG. 14 is a schematic view of a user input interface from the remote control device, according to the present disclosure.

Referring now additionally to FIG. 14, the remote control device 101 includes a user input interface 104 coupled to the second processor 103 (i.e. the second processor operatively renders the user input interface on the display 102). The second processor 103 is configured to generate the plurality of target values for application of the ophthalmic laser device 115 based upon input from the user input interface 104. In the illustrated embodiment, the user input interface 104 comprises a software user interface 790 comprising a omnidirectional input 791, a plurality of video feeds 792a-792b, a plurality of control inputs 793a-793g, and a stop command button 794.

Moreover, the examination device 110 illustratively includes a robotic device defining a robotic arm 113 coupled to the first processor 112 (i.e. operatively coupled so that the first processor controls circuitry driving the robotic arm), and a lens coupled to a distal end of the robotic arm. The first processor 112 is configured to position the lens via the robotic arm 113. The first processor 112 is configured to position the lens based upon input from the remote control device 101. The first processor 112 is configured to receive at least one laser parameter for the plurality of target values for application of the ophthalmic laser device 115 from the remote control device 101. The at least one laser parameter may comprise a pulse type pulse duration, a laser source power, and a size of collimated beam, for example.

Another aspect is directed to a method for making a remote ophthalmic system 100. The method may include providing an examination device 110 comprising an ophthalmic laser device 115, and a first processor 112 coupled to the ophthalmic laser device, and providing a remote control device 101 to be associated with a user 105, to be remote to the examination device, and to be in communication with the examination device 110 over a communication network 116. The first processor 112 is configured to receive a plurality of target values for application of the ophthalmic laser device 115 from the remote control device 101, the plurality of target values for application of the ophthalmic laser device being associated with at least one ophthalmic procedure on a patient 114, and perform the at least one ophthalmic procedure on the patient by applying the ophthalmic laser device based upon the plurality of target values.

Figure 6:
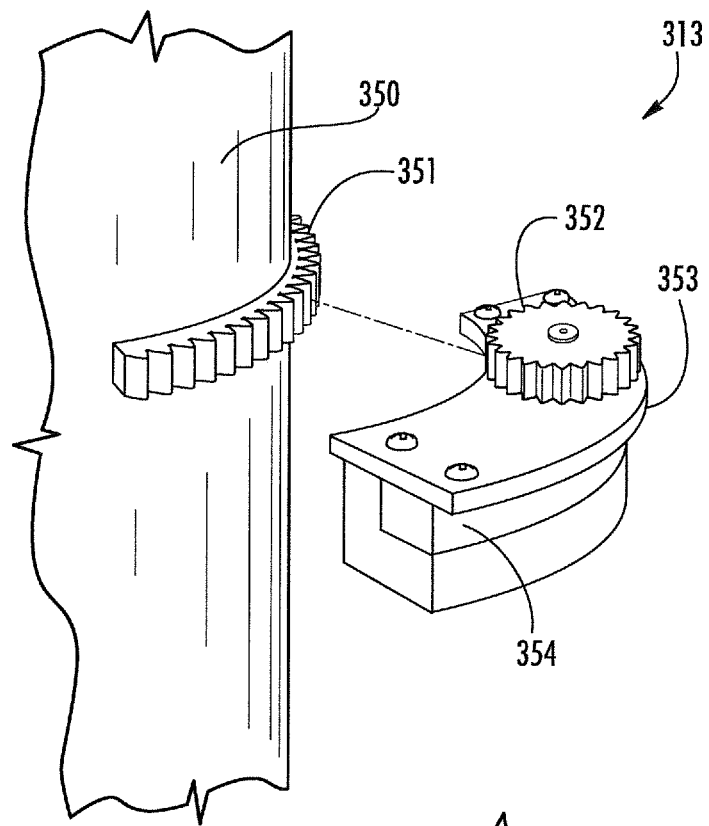
FIGS. 6-7 are perspective views of another embodiment of the robotic device from the examination device, according to the present disclosure.
Figure 7:
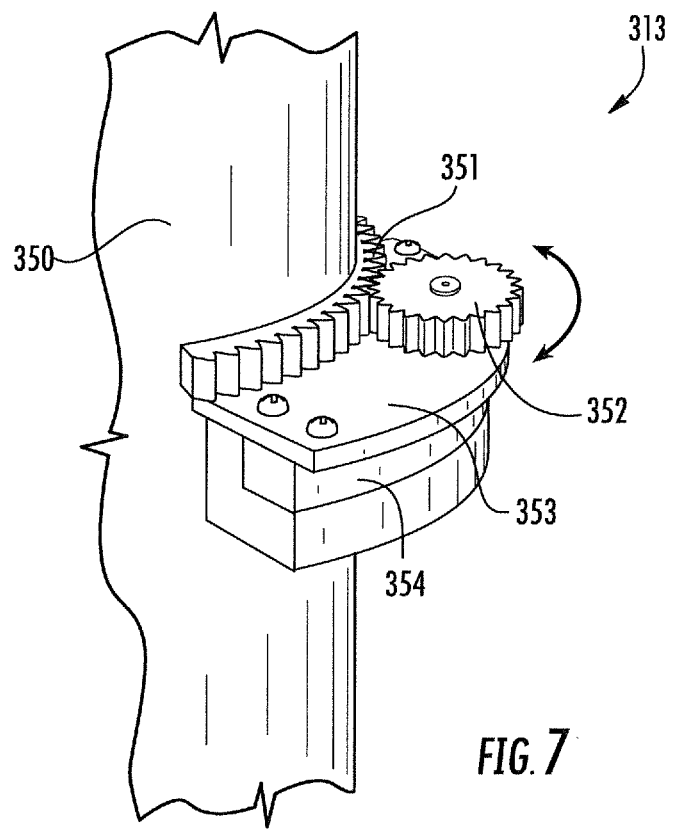

Referring now additionally to FIGS. 6-7, another embodiment of the robotic device 313 is now described. In this embodiment of the robotic device 313, those elements already discussed above with respect to FIG. 1 are incremented by 200 and most require no further discussion herein. This embodiment differs from the previous embodiment in that this robotic device 313 comprises a motorized slit lamp device component or other similar component comprising of an illuminating device and an imaging device. In particular, the robotic device 313 illustratively includes a housing 350, and a geared interface 351 carried by the housing.

As will be appreciated by the skilled person, the typical slit lamp comprises a plurality of manual adjustment mechanisms, the local operator engaging the plurality of manual adjustment mechanisms (e.g. knobs) to fit the patient. The geared interface 351 is part of one of the plurality of manual adjustment mechanisms. Rather than the typical manual driver (e.g. knob), which is removed, the robotic device 313 illustratively includes a frame 353 carried by the housing 350, and an electric motor 354 carried by the frame, and a gear 352 operatively coupled to the electric motor and driving the geared interface 351. In this embodiment, the motorized slit lamp device component is used for retrofit applications, i.e. converting typical slit lamp devices into motorized slit lamp devices used in the remote ophthalmic system 100. The first processor (not shown) is configured to actuate the electric motor 354 via commands received from the remote control device (not shown).

In this embodiment, the base of the slit lamp device may also be motorized. So, the user of the remote control device can position the examination device (i.e. slit lamp device). The examination device may include a plurality of omniwheels (e.g. four) mounted on two transverse shafts for allowing respectively for left-right and back-forth movement of the slit lamp device base on the table. This raises the base of the slit lamp device off of the table by up to a couple of inches. As a result, the tracks on either side should be raised appropriately so that the slit lamp device is not able to be moved off of the table, either by manual force or use of the motors. A double-shafted motor or servo moves each axle with an omni-wheel mounted on each end of the axles. Omni-wheels have rollers so that the wheels can be passively moved in a perpendicular angle from normal active-motion by the alternate drive shaft. In other embodiments, mecanum wheels could be used, though with different angular placement, or passive rollers could be used allowing the use of only two omni-wheels underneath to save on cost, though this isn't the preferred method of installation.

In this embodiment, motors, wires, sensors, etc. are nearly all mounted on the outside of the slit lamp device in order to facilitate fit and ease of adjustments, alterations and repairs. It is not intended that this embodiment be used for production models, except in the possible cases were a retrofit of specific models are desired (e.g. for a group of doctors fond of a particular model of slit lamp device that cannot be specially manufactured with the robot components integrated from the start). This embodiment may advantageously lower costs for organizations that already have slit-lamps and could also be used to create lower cost robotic slit-lamps for poorer populations since donated used equipment could be used. This embodiment may require that covers (not shown) be produced out of plastic, metal, fabric, or silicone, for example, in order to hide/shield the motors and wires and keep them from easy patient access. These covers are to be custom-built in each instance to fit as close to the slit-lamp as possible without hindering movement.

Figure 8:
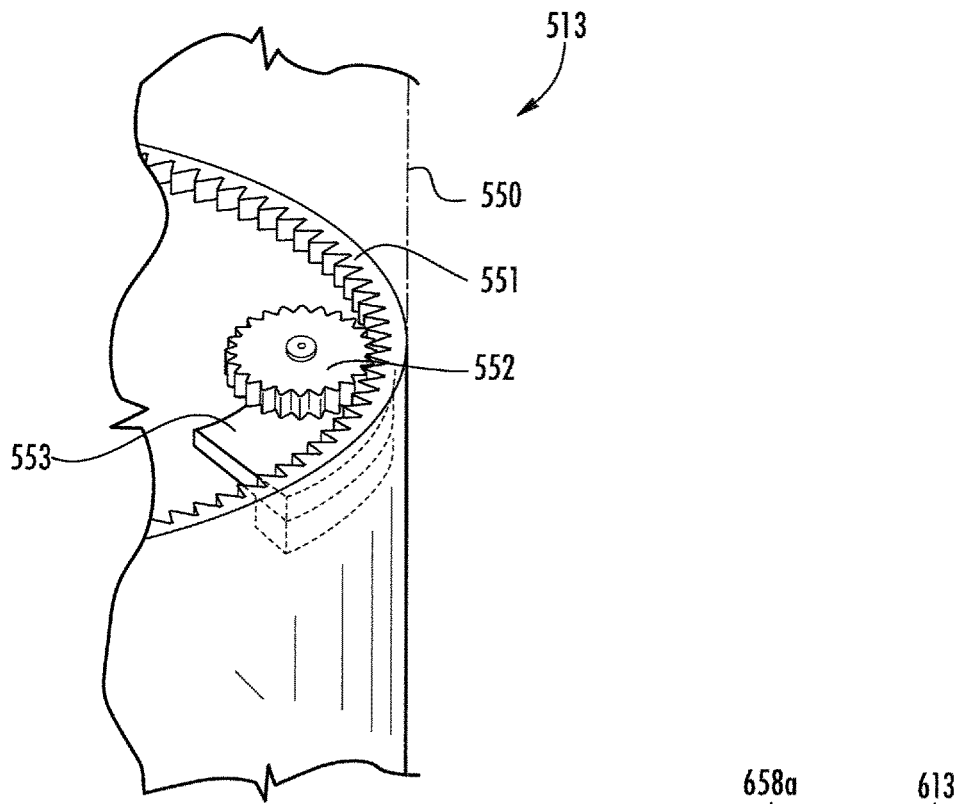
FIG. 8 is a perspective view of another embodiment of the robotic device from the examination device, according to the present disclosure.

Referring now additionally to FIG. 8, another embodiment of the robotic device 513 is now described. In this embodiment of the robotic device 513, those elements already discussed above with respect to FIG. 1 are incremented by 400 and most require no further discussion herein. This embodiment of the robotic device 513 comprises a motorized slit lamp device component. In particular, the robotic device 513 illustratively includes a housing 550, a frame 553 carried internally by the housing, and a geared interface 551 carried internally by the housing. In this embodiment, the motorized slit lamp device component is installed during manufacture of the slit lamp device.

In this embodiment, the motors, wires, sensors, etc. are nearly all mounted on the inside of the slit lamp device. A slit lamp device would be produced (and dimensions altered, if necessary) so that small geared motors fit inside the interior compartments with geared inserts at the joints to allow movement.

Figure 9:
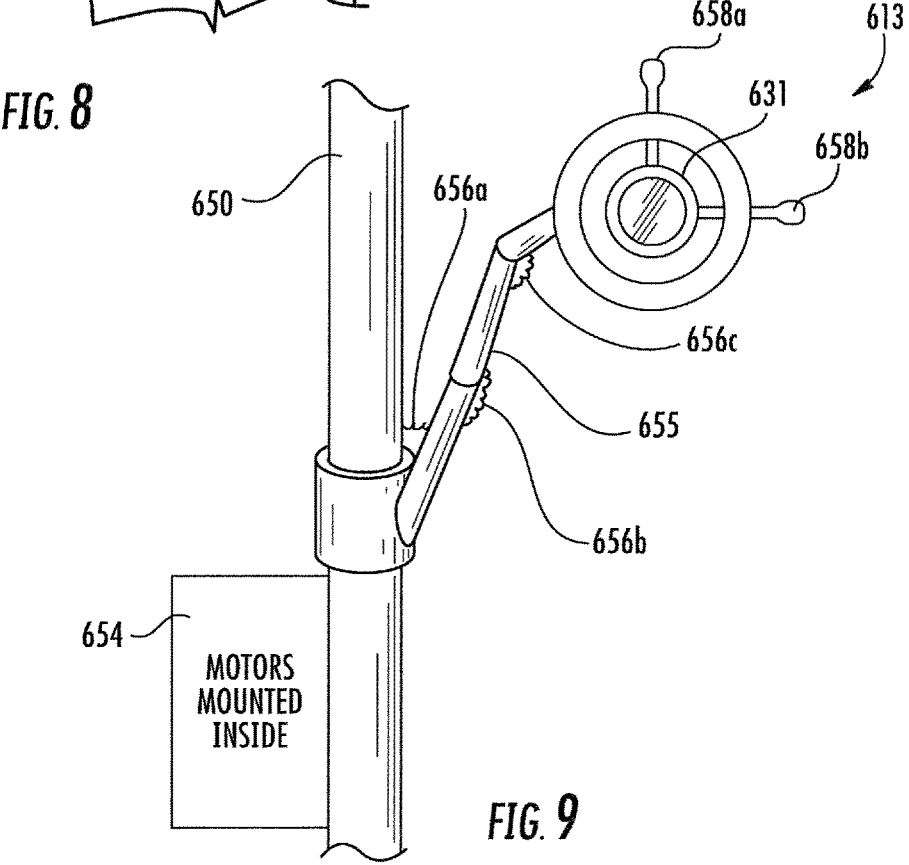
FIGS. 9-10 are perspective views of another embodiment of the robotic device from the examination device, according to the present disclosure.
Figure 10:
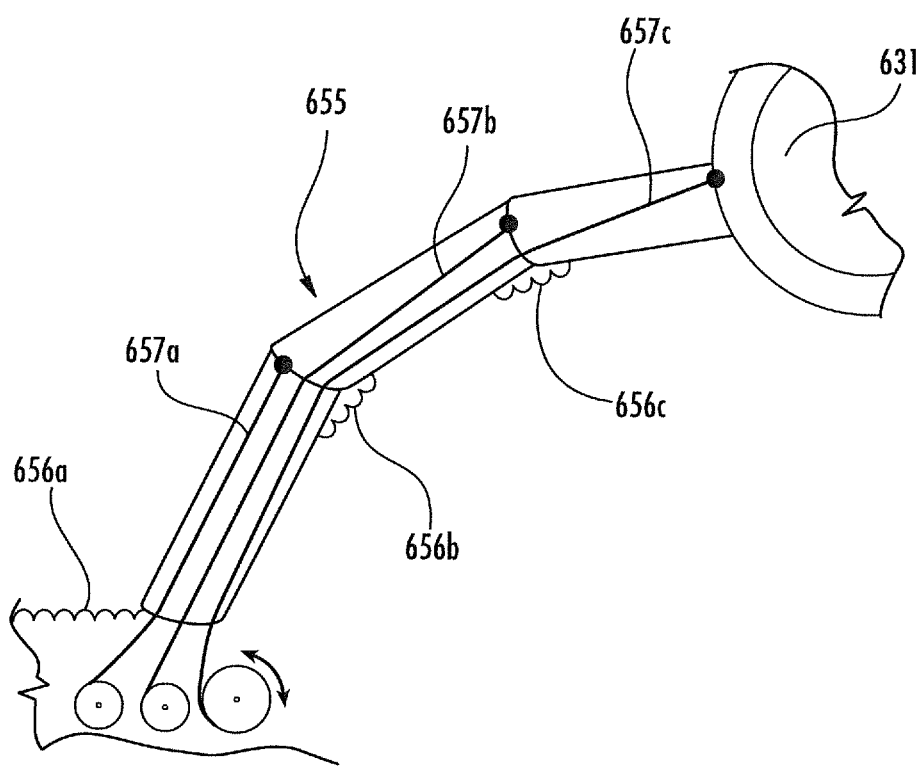

Referring now additionally to FIGS. 9-10, another embodiment of the robotic device 613 is now described. In this embodiment of the robotic device 613, those elements already discussed above with respect to FIG. 1 are incremented by 500 and most require no further discussion herein. This embodiment differs from the previous embodiment in that this robotic device 613 comprises a robotic arm. The robotic device 613 illustratively includes a housing (e.g. the illustrated post) 650, an electric motor 654 coupled to the housing, an arm 655 having a plurality of arm segments, a plurality of spring members 656a-656c coupled between the plurality of arm segments, and a lens 631 carried by a distal portion of the arm. The robotic device 613 illustratively includes a plurality of retaining screws 658a-658b fixing the lens 631 to the distal portion of the arm 655. The arm 655 illustratively includes a plurality of retractable cables 657a-675c configured to extend and retract the plurality of arm segments.

The lens holder allows for robotic adjustment of the position so that appropriate areas of the retina, as well as any other area of the eye that the physicians wishes to view, can be brought into focus for examination and surgery. The appropriate lens must be manually attached (via the plurality of retaining screws 658a-658b or other secure method of attachment) into the end holder by the on-site medical assistant. A coupling agent between the lens and eye is also applied manually as the lens is manually moved into the appropriate general position. At that point, robotic control is used to make minute adjustments in the position of the lens.

In order to keep the lens holder light and minimize obstruction in front of the patient's eye and face, indirect drives are recommended for actuation. In other embodiments, the arm 655 could alternatively include a plurality of small electric motors respectively driving each arm segment. In these embodiments, the arm 655 could comprise a robotic arm, as available from the Fanuc America Corporation of Rochester Hills, Mich. A lens holder is needed on both sides to be mounted to the chin-rest bars or a doubled chin-rest can be used so that the lens holder is in a stationary position. One side is the mirror-image of the other if the lens holder is duplicated (only one side is shown in the drawings below).

In the indirectly-driven model, a tendon 657a-657c attaches to each joint. These tendons 657a-657c are usually strong strings or lubricated metal cables. The cables are routed through the arm 655 with more tendons 657a-657c being present as one nears the base of the robotic arm. Each tendon 657a-657c is mounted to a motor shaft were the rotation of the shaft winds or unwinds the tendon. This changes the tendon length and also the tension it exerts at joint, causing the joint to move. This only works in one direction, so springs 656a-656c are used as counter tension. In the illustrated embodiment, the arm 655 comprises springs 656a-656c in as a functional model, but other embodiments have flexible joints made from pretension material to act as the spring). The springs 656a-656c also help to passively keep the lens 631 on the eye as the patient moves slightly during the procedure. This type of drive mechanism is known as cable-driven, tendon-driven, and sometimes a type of Bowden driven mechanism.

Figure 11:
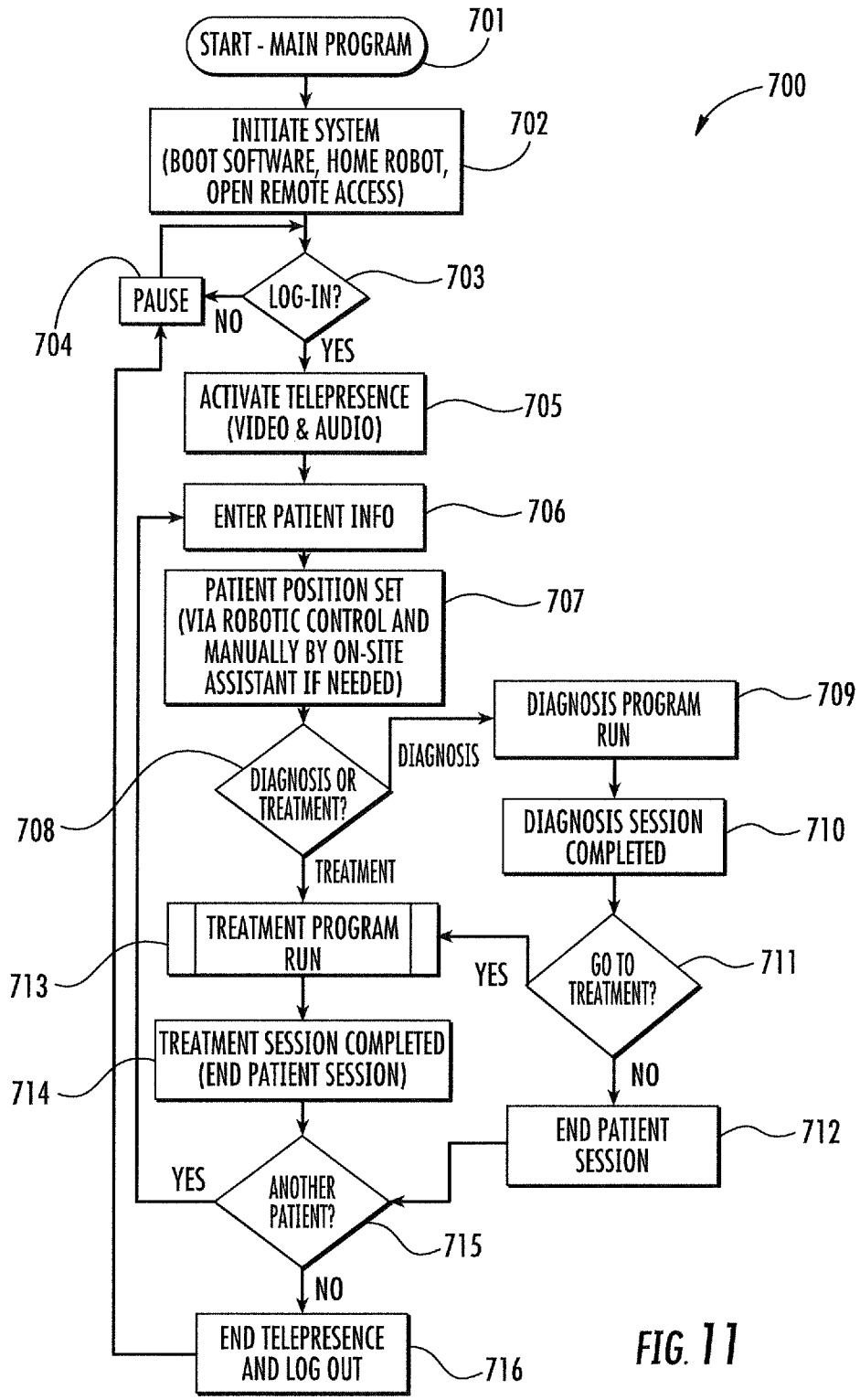
FIGS. 11-13 are flowcharts illustrating operation of the remote ophthalmic system of FIG. 1.
Figure 12:
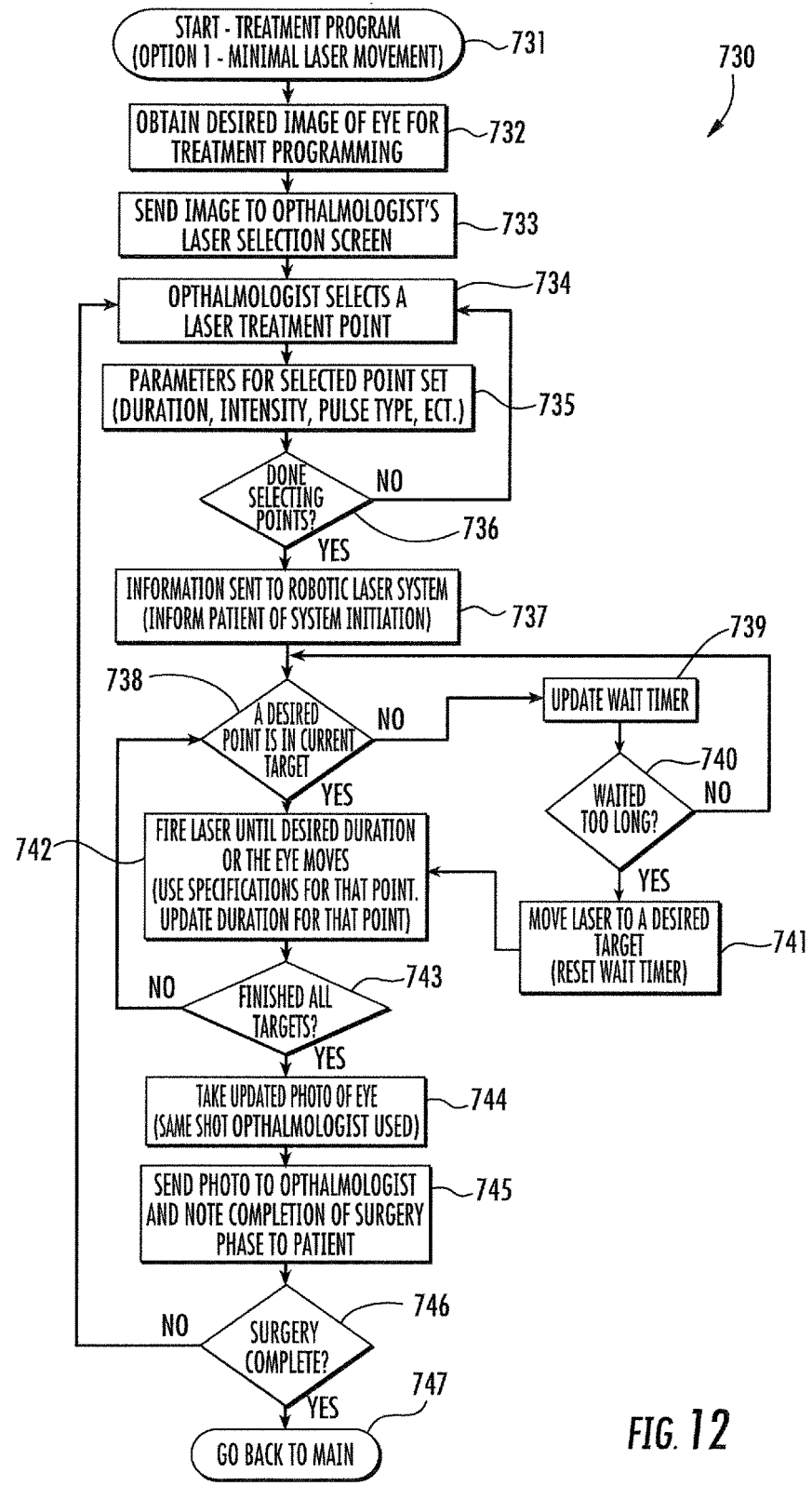
Figure 13:
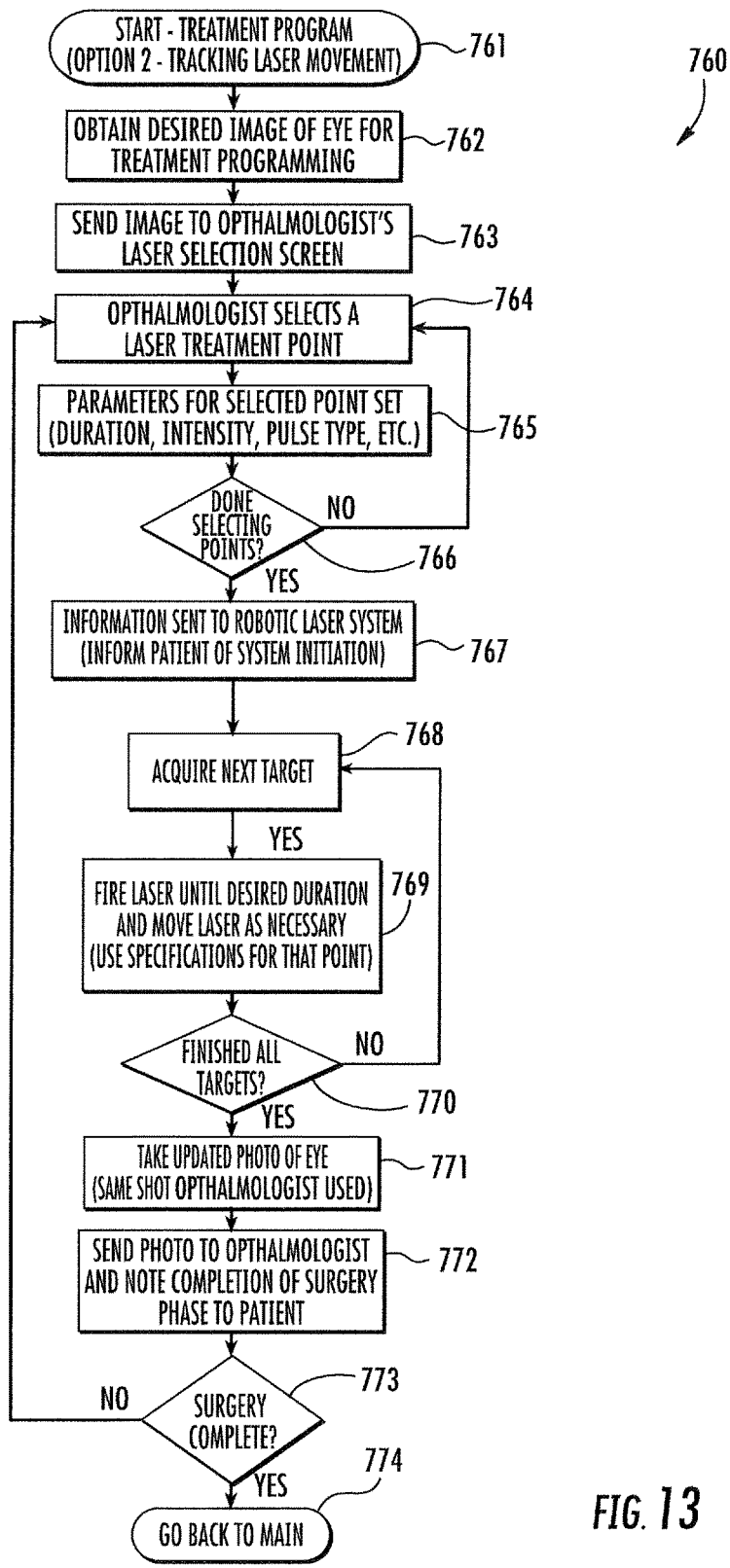

Referring now additionally to FIGS. 11-13, a flowchart 700 begins with Block 701 and illustrates control of the software for the remote control device 101. In particular, Blocks 702-707 relate to system boot-up; Blocks 708-712 relate to patient diagnosis; Blocks 708, 713-716 relate to patient treatment. In flowchart 730, the process for patient treatment in the remote ophthalmic system 100 is described. Blocks 731-733 relate to retrieving an image of the eye of the patient. Blocks 734-736 relate to selection of the plurality of target values for application of the ophthalmic laser device 115. Blocks 737-743 relate to the transmission of the selection of the plurality of target values to the examination device 110 and the execution of the at least one ophthalmic procedure on the patient 114. Blocks 744-747 relate transmission of an update final image of the eye of the patient 114, and ending of the at least one ophthalmic procedure.

In flowchart 760, the process for operation of a treatment program in the examination device 110 is now described. Blocks 761-766 to selection of the plurality of target values for application of the ophthalmic laser device 115. Blocks 767-770 relate to the transmission of the selection of the plurality of target values to the examination device 110 and the execution of the at least one ophthalmic procedure on the patient 114. Blocks 771-774 relate transmission of an update final image of the eye of the patient 114, and ending of the at least one ophthalmic procedure.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the present disclosure.

That which is claimed is:

1. A remote ophthalmic system comprising:
an examination device comprising
a microscope,
a first processor coupled to said microscope,
at least one robotic arm coupled to said first processor,
an ophthalmic laser device cooperating with said microscope, and
a lens coupled to a distal end of said at least one robotic arm and comprising one of a gonioscopy lens and a transequator lens, the at least one of the gonioscopy lens and the transequator lens to direct said ophthalmic laser device to different areas in an eye of a patient which are not accessible without the use of said lens;

a communication network; and
a remote control device being associated with a user, being remote to said examination device, and being in communication with said examination device over said communication network;
said first processor configured to
receive a plurality of target values for application of said ophthalmic laser device from said remote control device, the plurality of target values for application of said ophthalmic laser device being associated with at least one ophthalmic procedure on a patient, and
perform the at least one ophthalmic procedure on the patient by applying said ophthalmic laser device based upon the plurality of target values, and by positioning said lens via said at least one robotic arm onto an eye of the patient to direct a laser beam from said ophthalmic laser device into portions of the eye of the patient.

2. The remote ophthalmic system of claim 1 wherein said examination device comprises an image sensor device coupled to said first processor and configured to generate image data associated with the eye of the patient; and wherein said first processor is configured to transmit the image data to said remote control device.

3. The remote ophthalmic system of claim 2 wherein said remote control device comprises a display, and a second processor coupled to said display; and wherein said second processor is configured to receive the image data, and display the image data on said display.

4. The remote ophthalmic system of claim 3 wherein said remote control device comprises a user input interface coupled to said second processor; and wherein said second processor is configured to generate the plurality of target values for application of said ophthalmic laser device based upon input from said user input interface.

5. The remote ophthalmic system of claim 4 wherein the user input interface comprises a directional input, at least one video feed, and a plurality of control inputs.

6. The remote ophthalmic system of claim 1 wherein said first processor is configured to position said lens based upon input from said remote control device.

7. The remote ophthalmic system of claim 1 wherein said first processor is configured to receive at least one laser parameter for the plurality of target values for application of said ophthalmic laser device from said remote control device.

8. The remote ophthalmic system of claim 7 wherein the at least one laser parameter comprises, a pulse type, a pulse duration, a laser source power, and a size of collimated beam.

9. A remote ophthalmic system comprising:
an examination device comprising
a microscope,
a first processor coupled to said microscope,
a laser device cooperating with the microscope, and
an image sensor device coupled to said first processor and configured to generate image data associated with an eye of a patient,
at least one robotic arm coupled to said first processor, and
a lens coupled to a distal end of said at least one robotic arm and comprising one of a gonioscopy lens and a transequator lens, the at least one of the gonioscopy lens and the transequator lens to direct said laser device to different areas in an eye of a patient which are not accessible without the use of said lens;
a communication network; and
a remote control device being associated with a user, being remote to said examination device, and being in communication with said examination device over said communication network;
said first processor configured to
transmit the image data to said remote control device,
receive a plurality of target values for application of said laser device from said remote control device, the plurality of target values for application of said laser device being associated with at least one ophthalmic procedure on the patient, and
perform the at least one ophthalmic procedure on the patient by applying said laser device based upon the plurality of target values, and by positioning said lens via said at least one robotic arm onto the eye of the patient to direct a laser beam from said laser device into portions of the eye of the patient.

10. The remote ophthalmic system of claim 9 wherein said remote control device comprises a display, and a second processor coupled to said display; and wherein said second processor is configured to receive the image data, and display the image data on said display.

11. The remote ophthalmic system of claim 10 wherein said remote control device comprises a user input interface coupled to said second processor; and wherein said second processor is configured to generate the plurality of target values for application of said laser device based upon input from said user input interface.

12. The remote ophthalmic system of claim 11 wherein the user input interface comprises a directional input, at least one video feed, and a plurality of control inputs.

13. The remote ophthalmic system of claim 10 wherein said first processor is configured to position said lens based upon input from said remote control device.

14. The remote ophthalmic system of claim 10 wherein said first processor is configured to receive at least one laser parameter for the plurality of target values for application of said laser device from said remote control device.

15. A method for making a remote ophthalmic system comprising:
providing an examination device comprising
a microscope,
a first processor coupled to the microscope,
at least one robotic arm coupled to the first processor,
an ophthalmic laser device cooperating with the microscope, and
a lens coupled to a distal end of the at least one robotic arm and comprising one of a gonioscopy lens and a transequator lens, the at least one of the gonioscopy lens and the transequator lens to direct the ophthalmic laser device to different areas in an eye of a patient which are not accessible without the use of the lens; and
providing a remote control device to be associated with a user, to be remote to the examination device, and to be in communication with the examination device over a communication network;
the first processor configured to
receive a plurality of target values for application of the ophthalmic laser device from the remote control device, the plurality of target values for application of the ophthalmic laser device being associated with at least one ophthalmic procedure on a patient, and
perform the at least one ophthalmic procedure on the patient by applying the ophthalmic laser device based upon the plurality of target values, and by positioning the lens via the at least one robotic arm onto an eye of the patient to direct a laser beam from the ophthalmic laser device into portions of the eye of the patient.

16. The method of claim 15 wherein the examination device comprises an image sensor device coupled to the first processor and configured to generate image data associated with the eye of the patient; and wherein the first processor is configured to transmit the image data to the remote control device.

17. The method of claim 16 wherein the remote control device comprises a display, and a second processor coupled to the display; and wherein the second processor is configured to receive the image data, and display the image data on the display.

18. The method of claim 17 wherein the remote control device comprises a user input interface coupled to the second processor; and wherein the second processor is configured to generate the plurality of target values for application of the ophthalmic laser device based upon input from the user input interface.

19. The method of claim 18 wherein the user input interface comprises a directional input, at least one video feed, and a plurality of control inputs.

* * * * *